United States Patent [19]

Middle et al.

[11] Patent Number: 5,490,860
[45] Date of Patent: Feb. 13, 1996

[54] PORTABLE POWER CUTTING TOOL

[75] Inventors: George H. Middle, Reno; Edward A. Evans; Craig Purdy, both of Sparks, all of Nev.

[73] Assignee: Sofamor Danek Properties, Inc., Memphis, Tenn.

[21] Appl. No.: 163,999

[22] Filed: Dec. 8, 1993

[51] Int. Cl.$^6$ .................................................. A61B 17/32
[52] U.S. Cl. ................................................ 606/171; 604/22
[58] Field of Search ........................... 606/80, 159, 167, 606/170, 171, 180; 604/22

[56] References Cited

U.S. PATENT DOCUMENTS

| | | | |
|---|---|---|---|
| 3,835,858 | 9/1974 | Hagen | 606/180 |
| 4,203,444 | 5/1980 | Bonnell et al. | |
| 4,210,146 | 7/1980 | Banko | 606/171 |
| 4,246,902 | 1/1981 | Martinez | 606/171 |
| 4,461,305 | 7/1984 | Cibley | 606/180 |
| 4,589,414 | 5/1986 | Yoshida et al. | 604/22 |
| 4,705,038 | 11/1987 | Sjostrom et al. | |
| 4,771,774 | 9/1988 | Simpson et al. | 606/171 |
| 4,784,636 | 11/1988 | Rydell | 606/159 |
| 4,932,935 | 6/1990 | Swartz | 606/171 |
| 4,936,845 | 6/1990 | Stevens | 606/171 |
| 5,077,506 | 12/1991 | Krause. | |
| 5,112,299 | 5/1992 | Pascaloff | 606/180 |
| 5,133,729 | 7/1992 | Sjostrom. | |

FOREIGN PATENT DOCUMENTS 961686  9/1982  U.S.S.R. ............................ 606/180

*Primary Examiner*—Stephen C. Pellegrino
*Assistant Examiner*—Nancy Mulcare
*Attorney, Agent, or Firm*—Woodard, Emhardt, Naughton Moriarty & McNett

[57] ABSTRACT

A portable power cutting tool is disclosed, having a plurality of replaceable tool assemblies for connection to the power cutting tool, with each tool assembly having a different cutting blade and a mode of motion selected for optimum operation of the cutting blade. Each tool assembly has a mode of motion selected from the group of rotation, reciprocation, and a combination of rotation and reciprocation. The tool assemblies can be disposable.

5 Claims, 4 Drawing Sheets

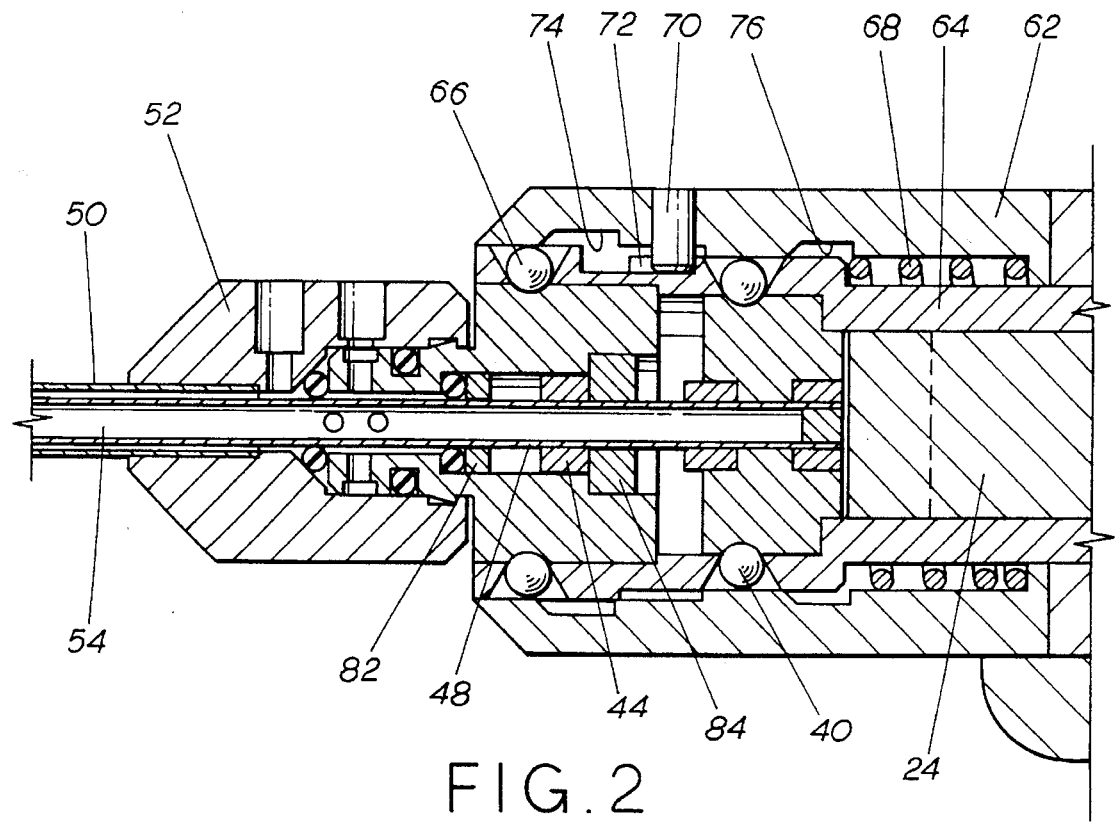
FIG.2
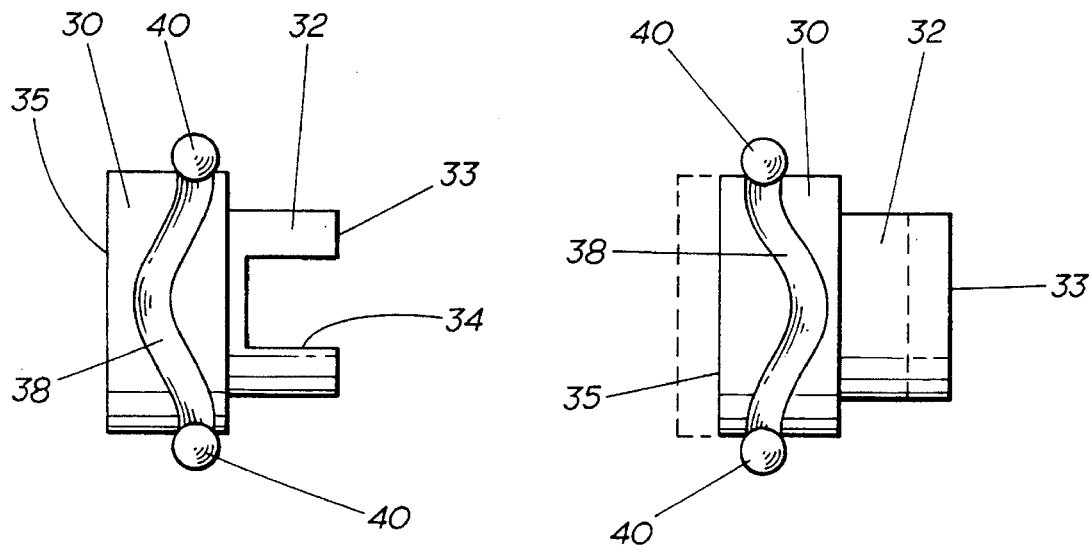
FIG.3
FIG.4

PORTABLE POWER CUTTING TOOL

TECHNICAL FIELD

This invention is in the field of power operated tools used during surgery for cutting, drilling, and similar functions, as applied to muscle, bone, or other types of tissue.

BACKGROUND OF THE INVENTION

During the performance of endoscopic or arthroscopic surgery, it is often necessary or useful to be able to perform a power assisted cutting, drilling, chipping, or other similar action on a variety of tissues. Such actions may be applied to muscle tissue, other soft tissue, or bone. The type of knife or other implement used for each function is specifically designed for the given type of action to be performed on a given type of tissue. Similarly, the motion which is imparted to the implement is designed to operate the specific implement in the preferred way. The mode of motion used in known power tools is either pure rotation or pure reciprocation.

For instance, the implement could be a drill, a scalpel, a burr, a rasp, a chisel, a rotary cutter, or a reciprocating cutter. The particular implement selected might perform better with a rotary action, or a reciprocating action. The preferred action might depend upon the type of tissue being operated on, as well as upon the type of implement. For the sake of simplicity, the action performed by these implements often will be referred to herein generally as "cutting", it being understood that for some implements, the action might more accurately be described as chiseling, filing, or some other action.

Such a known power tool would be an integral tool which might typically incorporate a handle such as a pistol grip, a drive mechanism, and a sheath through which the cutting implement is driven. The sheath might be open ended, or it might have an enclosed end, with the integral cutting implement being exposed through a side window. It is currently known to select a power tool which incorporates the desired type of cutting implement, with the power tool being designed to impart the selected mode of motion to the implement. Each currently known tool is limited to imparting either a rotary mode or a reciprocating mode of motion, to the cutting implement.

Such currently known power tools are typically electrically powered through a cable attached to the handle, or pneumatically powered through a hose. The electric motor and other elements of the drive mechanism are specifically designed to impart a rotary mode of motion to the cutting implement, or to impart a reciprocating mode of motion to the implement. When the surgeon wishes to switch to a different cutting implement, he must switch to a different power tool which incorporates the desired implement, and which is designed to impart the desired mode of motion to the implement.

There are several disadvantages to the currently known power surgery tools. First, the surgeon must switch to a different power tool if he wishes to use a different cutting implement. This requires that a relatively large number of power tools be made available for an operation, adding to clutter in the operating room, and adding to the expense of the surgery. Second, sterilization of a large number of power tools adds to the cost of the surgery and further taxes the resources of the hospital. Third, the hospital must insure that it has on hand a large number of power tools in order to meet the needs experienced during a wide variety of surgical operations. Fourth, currently known power tools are capable of imparting only rotary or reciprocating motion to a cutting implement. Many implements perform optimally when given a combination of rotary and reciprocating motion.

Therefore, it is an object of the present invention to provide a portable power surgery tool in which a portion of the drive mechanism can be changed to switch from one mode of motion to another mode. It is a further object of the present invention to provide a portable power surgery tool in which the cutting implement and a portion of the drive mechanism can be replaced as a disposable unit, to switch from one implement which requires a given mode of motion to another implement which requires a second mode of motion. It is a still further object of the present invention to provide a portable power surgery tool which is capable of imparting a combination of rotary and reciprocating motion to a cutting implement. It is yet a further object of the present invention to provide a portable power surgery tool which is economical to make and easy to use.

SUMMARY OF THE INVENTION

A preferred embodiment of the present invention, by way of example only, is a portable power tool having a housing in the shape of a pistol grip. The housing contains a battery or small power cartridge, an electric motor with a rotating output shaft, a transmission mechanism, a drive shaft, a cutting implement on the drive shaft, and a sheath partially covering the drive shaft and the implement. The transmission mechanism, drive shaft, cutting implement and sheath can be removed and replaced easily with another similar assembly which incorporates a different cutting implement, and which imparts a different mode of motion to the implement. This assembly is designed to be disposable.

The transmission mechanism is driven by the rotating output shaft of the motor, and it converts this rotary motion to a given mode of output motion, which may be rotary, reciprocating or a combination of rotary and reciprocating. The type of output motion developed by a given transmission depends upon the design of a drive piston or bushing and a limiter piston or bushing within the transmission. The drive piston or bushing is driven in rotating motion by the output shaft of the motor. The drive piston or bushing is connected to the output shaft of the motor in such a way that the drive piston or bushing can move longitudinally with respect with the motor shaft, if necessary. If the desired output motion of the transmission is pure rotary motion, a drive bushing is used which has a smooth cylindrical outer surface, and it rotates within the housing of the tool, without any longitudinal motion.

On the other hand, if the desired output motion of the transmission has a reciprocating component, a drive piston is used or the outer surface of the drive piston is encircled with a continuous cam groove which bends toward one end of the piston and then toward the other end, such as a continuous sine wave. The tool has at least one cam follower element mounted within the housing so that the element will protrude into the cam groove in the drive piston. The element is captured so that it can not move with respect to the housing when the tool is assembled. Therefore, as the drive piston is rotated by the motor, the stationary element follows the continuous cam groove as the piston rotates, driving the piston back and forth longitudinally in a reciprocating motion. This element can be a ball or a pin, or some other element which will readily follow the cam groove.

A drive piston or bushing designed to produce motion having a rotary component is fixedly attached to the drive shaft, so that rotation of the drive piston or bushing results in rotation of the drive shaft. A drive piston designed to impart pure reciprocating motion to the cutting implement, with no rotary motion, is rotatably attached to the drive shaft, so that as the drive piston rotates, the drive shaft will not rotate.

Therefore, a drive piston designed to produce pure rotary motion will have no cam groove in its outer surface, and it will be fixedly attached to the drive shaft. A drive piston designed to produce a combination of rotary and reciprocating motion will have a cam groove in its outer surface, and it will be fixedly attached to the drive shaft. Finally, a drive piston designed to produce pure reciprocating motion will have a cam groove in its outer surface, and it will rotate freely with respect to the drive shaft.

At an intermediate point on the drive shaft, within a limiter piston cavity in the transmission body, a limiter piston or bushing is fixedly attached to the drive shaft. The limiter piston or bushing is specifically designed for the mode of motion desired for the attached cutting implement. The limiter piston cavity within the transmission body has a relatively square cross section in all cases. For a transmission designed to impart pure rotary motion to the cutting implement, the limiter bushing is cylindrical, with a diameter essentially equal to one side of the square cross section of the limiter piston cavity, so that the limiter bushing can rotate within the cavity as the drive piston rotates. The length of the limiter bushing is essentially equal to the length of the limiter piston cavity, preventing any longitudinal motion of the drive shaft which might result from causes such as vibration. This type of limiter bushing is referred to as a reciprocation limiter because it allows rotation but limits reciprocation.

For a transmission designed to impart pure reciprocating motion to the cutting implement, the limiter piston is relatively square in cross section, substantially matching the square cross section of the limiter piston cavity. This prevents any rotary motion of the drive shaft which might result from vibration. The length of the piston is somewhat less than the length of the limiter piston cavity, allowing longitudinal motion of the drive shaft which results from reciprocation of the drive piston. This type of limiter piston is referred to as a rotation limiter because it allows reciprocation but limits rotation.

For a transmission designed to impart a combination of rotary and reciprocating motion to the cutting implement, the limiter piston is cylindrical, with a diameter essentially equal to one side of the square cross section of the limiter piston cavity, so that the limiter piston can rotate within the cavity as the drive piston rotates. The length of the limiter piston is somewhat less than the length of the limiter piston cavity, allowing longitudinal motion of the drive shaft which results from reciprocation of the drive piston. This type of limiter piston is referred to as a free wheeling limiter because it allows reciprocation and rotation.

The drive shaft of each transmission mechanism has affixed to its distal end a cutting element, such as a scalpel, drill, burr, osteotome, or other implement. The drive shaft and cutting implement are encased within a rigid sheath, which is attached to the transmission body by means of a sheath housing. The sheath can have an open distal end, with the cutting implement protruding from the opening, or the sheath can have a window in its side, through which the cutting implement is exposed.

Irrigation fluid can be supplied to an irrigation port on the sheath housing and routed through the transmission body to the interior of the hollow drive shaft through holes in the drive shaft wall, within the transmission body. The irrigation fluid can be supplied to the treatment area via the transmission body and the drive shaft, to remove cut material from around the cutting implement. An aspiration tube can be connected to an aspiration port on the sheath housing, which is connected to a passageway through the housing to the interior of the sheath, outside the drive shaft. Irrigation fluid and other material can be aspirated from the area around the cutting implement via the sheath and the sheath housing.

If desired, the assembly consisting of the transmission body, drive shaft, cutting implement, sheath housing and sheath, referred to herein as the disposable surgical implement assembly, can be removed and replaced as a disposable unit, as described above, to switch from one cutting implement to another. Alternatively, the surgical implement assembly can be removed from the power tool, and the transmission body, drive shaft, drive piston or bushing, limiter piston or bushing, and cutting implement can be removed from the sheath and sheath housing. Then, the replacement transmission body, drive shaft, drive piston or bushing, limiter piston or bushing, and cutting implement can be installed in the sheath housing and sheath, and the whole surgical implement assembly can be reinstalled in the power tool. As an added feature, most or all of the components in the surgical implement assembly can be made of plastic or other disposable materials, eliminating the need to sterilize reusable components.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 2 is a sectional view of a reciprocating drive mechanism for the portable power tool shown in FIG. 1, showing a rotation limiter piston;

FIG. 3 is an elevational view of a reciprocating drive piston of the portable power tool shown in FIG. 1, with the drive piston in the forward position;

FIG. 4 is an elevational view of the reciprocating drive piston shown in FIG. 3, with the drive piston in the rear position;

FIG. 10 is a partial sectional view of a rotary/reciprocating cutter, drive shaft and sheath for use on the portable power tool shown in FIG. 1.

DESCRIPTION OF PREFERRED EMBODIMENTS

Figure 1:
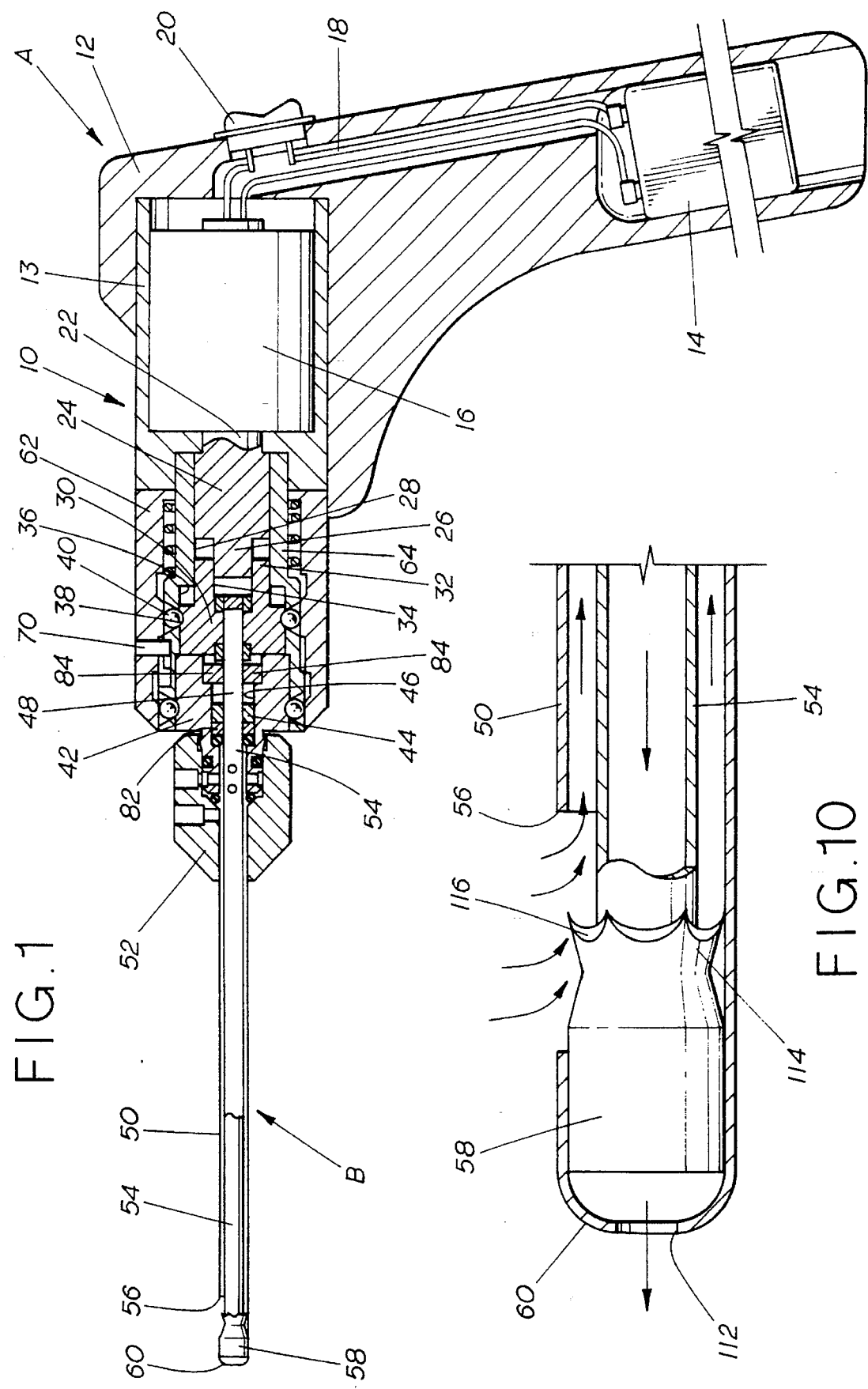
FIG. 1 is a sectional view of the portable power tool of the present invention.

Referring to FIG. 1, the portable power tool 10 of the present invention is comprised of handle assembly A and disposable surgical implement assembly B. Handle assembly A includes a handle housing 12, a motor housing 13, a quick release collar 62, and a drive mechanism sleeve 64. Handle housing 12 is in the shape of a pistol grip, with a battery 14 mounted inside. Handle housing 12 would typically be constructed of a molded plastic material. Motor housing 13 is a generally hollow, rigid housing mounted near the top of handle housing 12, with electric motor 16 inside, and oriented so that motor output shaft 22 extends in a forward direction from the handle housing, much like the barrel of a gun.

Electric motor 16 is preferably a direct current motor, connected to battery 14 by wires 18, and controlled by switch 20, accessibly mounted on handle housing 12. Electric motor 16 could also be wired for reversible operation. The forward end of motor output shaft 22 has fixedly mounted thereto a solid cylindrical drive mandrel 24. Drive mandrel 24 rotates about its longitudinal axis in drive mandrel cylinder 28, within sleeve 64. Formed on the forward end of drive mandrel 24 is a drive bushing tongue 26, which has two opposed flat surfaces.

The forward end of drive mandrel tongue 26 engages a drive slot 34 in the rear end of a solid cylindrical rod 32, which projects rearwardly from reciprocating drive piston 30. As motor 16 rotates drive mandrel 24, drive piston 30 rotates and reciprocates within cylinder 36. As will be explained later, reciprocating drive piston 30 can be removed and replaced with a drive piston that only rotates, if desired. A continuous cam groove 38 is formed in the outer surface of reciprocating drive piston 30, to interact with cam follower balls 40 to cause reciprocating drive piston 30 to reciprocate as it rotates. Instead of balls 40, a different cam follower element could be used, such as one or more cam follower pins (not shown) projecting radially inwardly through sleeve 64 into continuous cam groove 38.

Connected to and projecting forwardly from drive piston 30 is pilot section 48 of drive shaft 54. Rotation limiter piston 44 is fixedly mounted around drive shaft 54 near pilot section 48. As will be explained later, rotation limiter piston 44 can be removed and replaced with a limiter bushing which limits reciprocation, or with a free wheeling limiter piston. Rotation limiter piston 44 oscillates longitudinally within limiter piston cavity 46 within transmission body 42. Limiter piston cavity 46 has a transverse cross section that is substantially square, and rotation limiter piston 44 has a substantially square cross section which essentially matches the transverse cross section of limiter piston cavity 46, so that the limiter piston and drive shaft 54 can not rotate. Rotation limiter piston 44 has a length somewhat shorter than the longitudinal length of limiter piston cavity 46, so that the limiter piston 44 and drive shaft 54 can oscillate longitudinally.

Drive shaft 54 is a hollow rigid tube which projects forwardly from limiter piston 44, through sheath housing 52 and sheath 50. The rear end of drive shaft 54 in the embodiment shown in FIG. 1 is rotatably attached to drive piston 30, so that the reciprocating motion of drive piston 30 is imparted to drive shaft 54, but the rotary motion of drive piston 30 is not imparted. As will be explained later, alternate embodiments of drive piston 30 can be provided, which will either impart only rotary motion or impart both rotary and reciprocating motion. The forward end of drive shaft 54 has fixedly attached thereto a cutter 58, shown in FIG. 1 as a reciprocating cutter. Cutter 58 could also be a variety of other surgical implements, such as a drill, a burr, a chisel, or others. Cutter 58 is exposed to the tissue to be cut through window 56 in the side of sheath 50.

Referring now to FIG. 2, the drive mechanism of the power tool shown in FIG. 1 can be seen. Whereas FIG. 1 showed drive piston 30 and rotation limiter piston 44 in their forward positions, with limiter piston 44 abutting its forward stop ring 82, FIG. 2 shows drive piston 30 and limiter piston 44 in their rear positions, with limiter piston 44 abutting its rear stop ring 84. In both positions, pilot section 48 of drive shaft 54 extends through, and is guided by the central bore of rear limiter piston stop ring 84. Additional centralization of drive shaft 54 is achieved by the alignment of rod 32 within drive mandrel cylinder 28.

Drive mechanism sleeve 64 and quick release collar 62 are permanently mounted in handle assembly A, while drive piston 30, drive shaft 54, and transmission body 42 are removable therefrom along with the other components of disposable surgical implement assembly B. Drive mechanism sleeve 64 is fixedly attached to motor housing 13, while quick release collar 62 is slidably mounted on the outer surface of sleeve 64. Collar return spring 68 is positioned between opposed shoulders of sleeve 64 and collar 62 to continuously urge collar 62 rearwardly against motor housing 13.

Drive mechanism sleeve 64 is a generally cylindrical sleeve having three different inside diameters at drive mandrel cylinder 28, cylinder 36, and the forward bore of sleeve 64 which receives transmission body 42. There are at least two countersunk holes through the wall of sleeve 64 into its forward bore, alongside transmission body 42, to receive transmission retaining balls 66. Retaining balls 66 are of sufficient diameter to prevent their passage completely through the wall of sleeve 64, but to allow their partial projection into a retaining groove 78 on the outer surface of transmission body 42.

There are also two countersunk holes through the wall of sleeve 64 into cylinder 36, to receive cam follower balls 40. If cam follower pins were used instead of balls 40, as mentioned earlier, the pins could be received in straight, rather than countersunk, holes through sleeve 64. Cam follower pins, if used, could also have rounded inner ends, or be spring biased outwardly, to facilitate their entry into and exit from continuous cam groove 38. Cam follower balls 40 are of sufficient diameter to prevent their passage completely through the wall of sleeve 64, but to allow their partial projection into cam groove 38 on the outer surface of drive piston 30. Collar 62 is a generally hollow cylindrical collar which has an annular retaining ball release channel 74 around its inner surface near retaining balls 66, and an annular cam follower release channel 76 around its inner surface near cam follower balls 40.

When collar 62 is abutting motor housing 13, as shown, release channels 74, 76 are not aligned with retaining balls 66 and cam follower balls 40, so the balls are forced into the bottoms of their respective countersunk holes by the inner surface of collar 62. This causes retaining balls 66 to retain transmission body 42 within sleeve 64, and it causes cam follower balls 40 to project into cam groove 38 to impart reciprocating motion to drive piston 30 as it rotates. If cam follower pins were used instead of balls 40, the pins could have rounded outer ends to facilitate their entry into and exit from release channel 76. Abutment of collar 62 against motor housing 13 would then force the pins radially inwardly into cam groove 38 to impart reciprocating motion to drive piston 30.

A J-groove 72 is formed in the outer surface of sleeve 64, aligned with a lock pin 70 projecting inwardly from collar 62. Lock pin 70 interacts with J-groove 72 to lock collar 62 in a forward position which aligns release channel 74 with retaining balls 66 and aligns release channel 76 with cam follower balls 40. When channels 74, 76 are so aligned, balls 66, 40 are released to rise in their respective countersunk holes. This allows disposable surgical implement assembly B to be removed from handle assembly A and replaced with a different surgical implement assembly B, having a different surgical implement and a different mode of motion.

Referring now to FIGS. 3 and 4, the reciprocation of drive piston 30 can be more fully explained. Drive piston 30 is encircled by continuous cam groove 38, which has two bends nearer to the forward end 35 of piston 30, separated by two bends nearer the rear end 33 of piston 30. Keeping in mind that cam follower balls 40 are held in place with respect to handle assembly A, FIG. 3 shows piston 30 in a forward position, with balls 40 located in the rear bends of cam groove 38. FIG. 4 shows piston 30 after it has been rotated 90 degrees from the position shown in FIG. 3, by drive mandrel 24. Balls 40 are now located in the forward bends of cam groove 38, and piston 30 has been forced to its rear position. It can be seen that each complete revolution of piston 30 will cause piston 30 to go through two complete reciprocation cycles. Varying the number of forward and rear bends of cam groove 38 can vary the number of complete reciprocation cycles per revolution. As piston 30 reciprocates, slot 34 of piston 30 slides back and forth along tongue 26 of drive mandrel 24.

Figure 5:
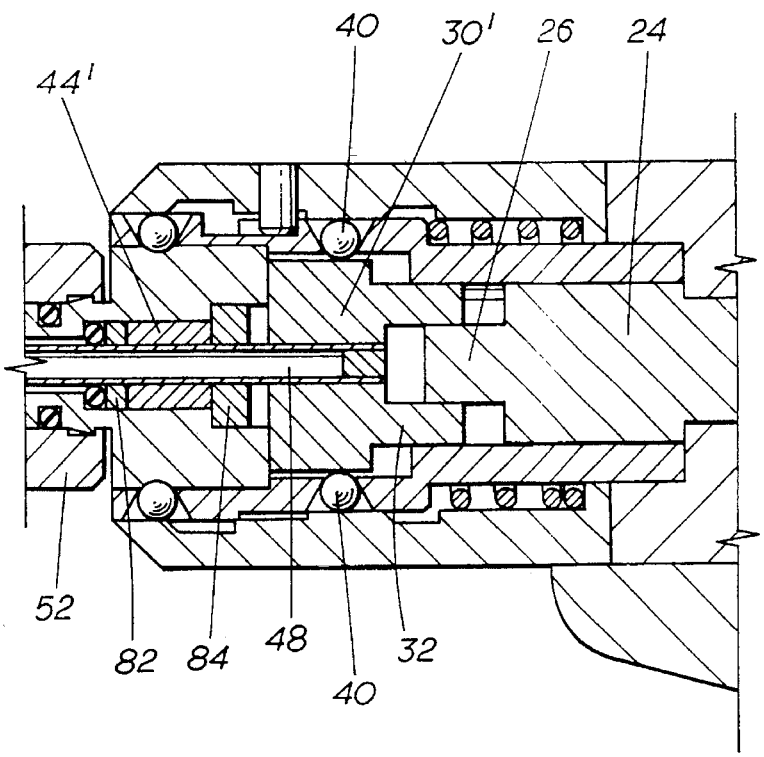
FIG. 5 is a sectional view of a rotary drive mechanism for the portable power tool shown in FIG. 1, showing a reciprocation limiter mandrel.

Referring now to FIG. 5, a drive mechanism can be seen which is designed to impart pure rotary motion to the surgical implement. Drive bushing 30' is shown without a cam groove, and cam follower balls 40 simply ride along the outer surface of bushing 30'. To allow balls 40 to bottom out in their countersunk holes, drive bushing 30' must have a slightly reduced outside diameter as compared to drive piston 30. Reciprocation limiter bushing 44' is a cylindrical piston with a diameter substantially equal to the length of a side of square cavity 46 in transmission body 42. Limiter bushing 44' has a length substantially equal to the length of cavity 46. Therefore, reciprocation limiter piston 44' rotates freely within cavity 46, but it can not reciprocate.

Figure 6:
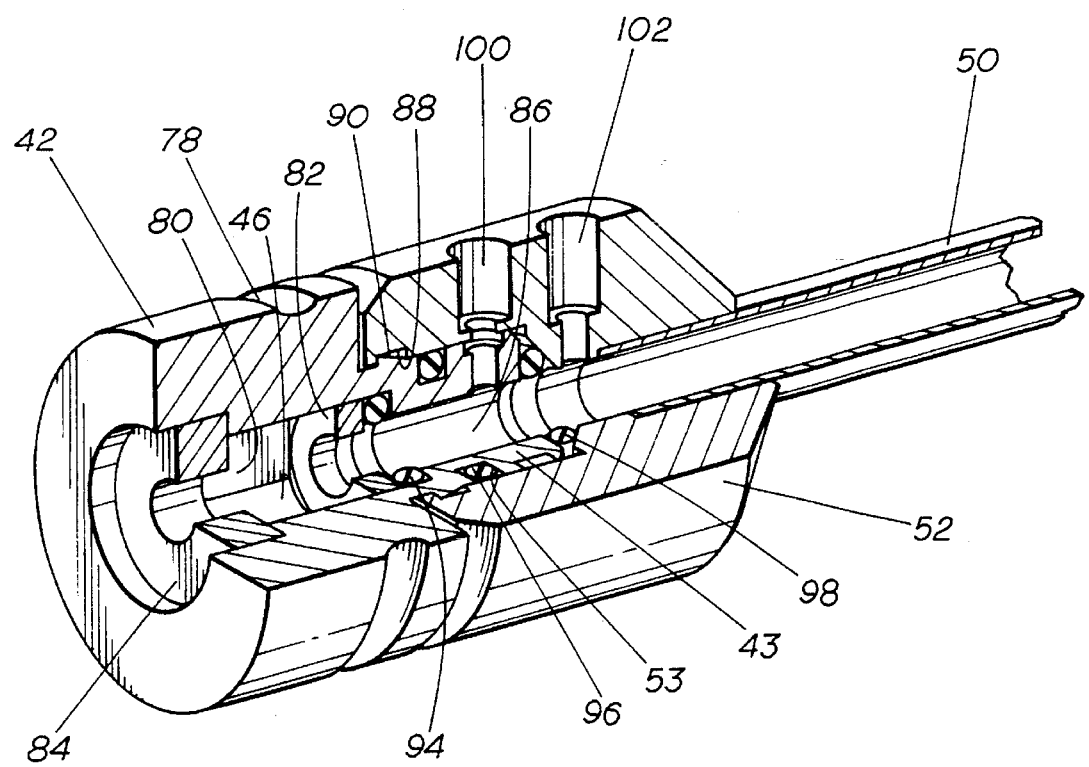
FIG. 6 is a cut away view of the transmission body and sheath of the portable power tool shown in FIG. 1.

Referring now to FIG. 6, the attachment of sheath housing 52 to transmission body 42 can be seen. Sheath housing 52 is a solid cylindrical body having a central longitudinal bore therethrough. Sheath 50 is fixedly attached to the forward end of sheath housing 52. Limiter piston cavity 46 within transmission body 42 is formed by four cavity walls 80, which meet in radiused corners, but which could meet in square corners. Cavity 46 has an essentially square transverse cross section, and an essentially rectangular longitudinal cross section. Forward stop ring 82 limits the forward travel of the limiter piston, while rear stop ring 84 limits the rearward travel of the limiter piston. Both stop rings 82, 84 are fixedly mounted in transmission body 42.

A neck 43 extends forward from transmission body 42 into the central bore of sheath housing 52, where it is locked in place by the engagement of latch 90 within latch groove 88 of sheath housing 52. Irrigation fluid can be supplied to irrigation port 100, to flow through irrigation passageway 86 in transmission body 42, and into the hollow drive shaft 54 as will be described later. A suction means can be attached to aspiration port 102, to aspirate material from the treatment area, up the sheath 50 on the outside of the drive shaft 54. Rear o-ring 94 seals between the transmission body 42 and the drive shaft 54, to prevent irrigation fluid from leaking back into the limiter piston cavity 46. Central o-ring 96 seals between the transmission body 42 and the sheath housing 52, to prevent irrigation fluid from leaking out to the atmosphere. Forward o-ring 98 seals between the transmission body 42, the sheath housing 52, and the drive shaft 54, to prevent a short circuit between the irrigation fluid and the aspirated material. The assembly shown in FIG. 6 is the same for all surgical implement assemblies, regardless of the mode of motion used.

Figure 7:
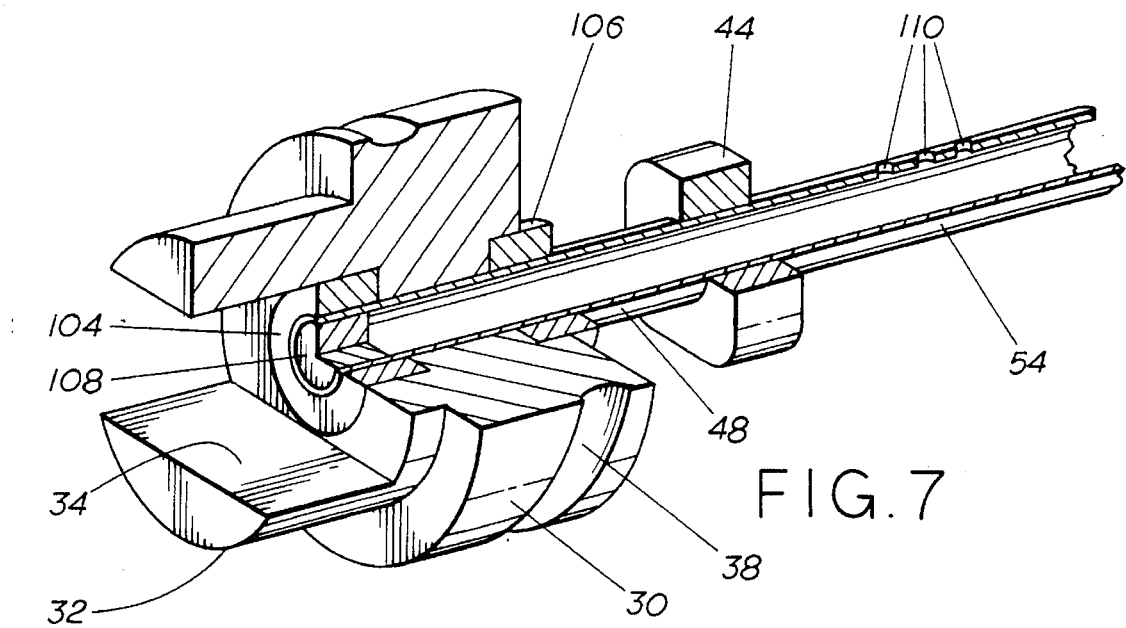
FIG. 7 is a cut away view of a reciprocating drive piston and rotation limiter piston for the portable power tool shown in FIG. 1.

FIG. 7 shows a drive piston 30 and limiter piston 44 designed to impart a pure reciprocating motion to the surgical implement. Drive piston 30 has cam groove 38 on its outer surface, so drive piston 30 will be forced to reciprocate as it is rotated by drive mandrel 24. Rear stop ring 104 and forward stop ring 106 are fixedly attached to the drive shaft 54, but the drive shaft 54 and stop rings 104, 106 are rotatably mounted in drive piston 30. This causes drive shaft 54 to reciprocate as drive piston 30 reciprocates, but drive shaft 54 is not rotated by drive piston 30. Rotation limiter piston 44 is fixedly attached to the drive shaft 54, and it has a transverse cross section which substantially matches the transverse cross section of cavity 46.

Therefore, limiter piston 44 can allow drive shaft 54 to reciprocate, but any rotation of drive shaft 54 which might be caused by vibration or by friction between drive piston 30 and stop rings 104, 106 is prevented. Irrigation holes 110 are provided through drive shaft 54 to allow irrigation fluid to flow forward through drive shaft 54. Rearward flow of irrigation fluid through drive shaft 54 is prevented by plug 108.

Figure 8:
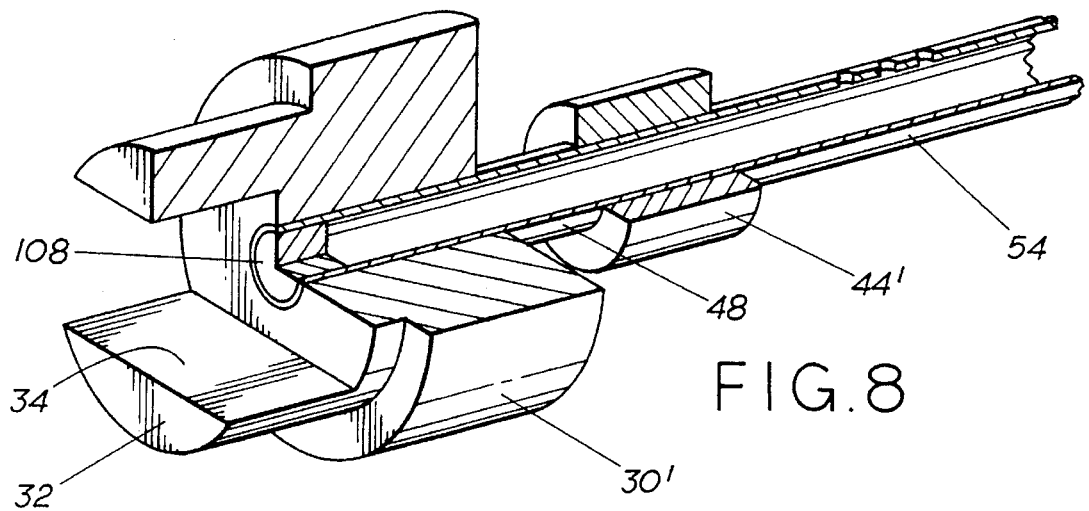
FIG. 8 is a cut away view of a rotary drive bushing and reciprocation limiter bushing for the portable power tool shown in FIG. 1.

FIG. 8 shows a drive bushing 30' and a limiter piston 44' designed to impart pure rotation to the surgical implement. It can be seen that drive bushing 30' has no cam groove, so drive bushing 30' will not be forced to reciprocate as it is rotated. Drive shaft 54 is fixedly attached to drive bushing 30', so rotation of drive piston 30' will result in rotation of drive shaft 54. Reciprocation limiter piston 44' has a round cross section with a diameter equal to the length of a side of the transverse cross section of cavity 46, so limiter bushing 44' can rotate within cavity 46. Reciprocation limiter bushing 44' has a length substantially equal to the longitudinal length of cavity 46, so any reciprocation that might be caused by vibration is prevented.

Figure 9:
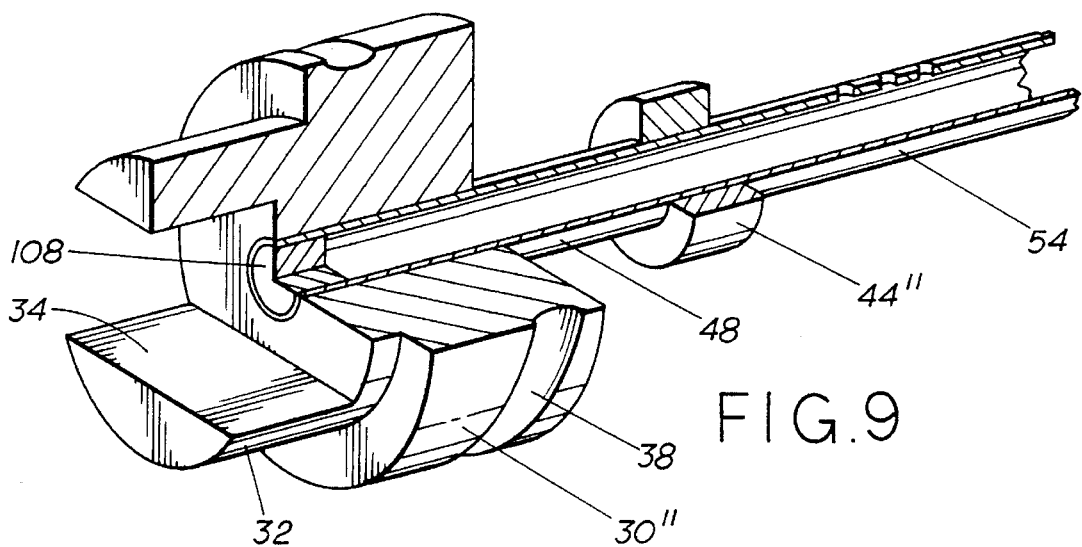
FIG. 9 is a cut away view of a rotary/reciprocating drive piston and free wheel limiter piston for the portable power tool shown in FIG. 1.

FIG. 9 shows a drive piston 30" and a limiter piston 44" designed to impart a combination of rotary and reciprocating motion to the surgical implement. Drive piston 30" has a cam groove 38 in its outer surface, so drive piston 30" will be forced to reciprocate as it is rotated. Drive shaft 54 is fixedly attached to drive piston 30", so both rotary and reciprocating motion will be imparted to drive shaft 54. Free wheeling limiter piston 44" has a round cross section like limiter piston 44' and a short length like limiter piston 44, so both rotary and reciprocating motion will be allowed.

FIG. 10 shows the arrangement of a cutter 58 near the distal end 60 of sheath 50. The particular cutter shown is specifically designed to work optimally with a mode of motion having a combination of rotary and reciprocating motion. Skirt 114 of cutter 58 has fluted cutting edges 116, which reciprocate and rotate to increase the exposure of tissue to the cutting edge and to aid in cleaning cut material from the cutting edge. Irrigation fluid flows forward along the inside of drive shaft 54, through cutter 58, and out orifice 112 in the distal end 60 of sheath 50. Aspirated material enters window 56 in the side of sheath 50 near cutter 58, and flows along the inside of sheath 50, on the outside of drive shaft 54, to the sheath housing 52 and the aspiration port 102.

OPERATION

As has been explained, rotation of drive piston 30 or drive bushing 30' or drive bushing 30", as the case may be, results in the desired mode of motion being imparted to the surgical implement installed. If it is desired to switch to a different surgical implement, with its preferred mode of motion, the disposable surgical implement assembly B being used is removed from handle assembly A, and replaced with the desired surgical implement assembly B having the desired different surgical implement attached.

When it is desired to remove disposable surgical implement assembly B from handle assembly A, in order to change to another surgical implement and another mode of motion, collar 62 is pulled forward against the resistance of return spring 68. This causes collar lock pin 70, projecting inwardly from collar 62, to pass along the longer leg of J-groove 72 in sleeve 64 to the curve of J-groove 72, at which time collar 62 is rotated slightly to cause lock pin 70 to enter the short leg of J-groove 72. Collar 62 can then be released, and it will remain in the forward, or release, position.

This allows disposable surgical implement assembly B to be removed and replaced with the desired assembly. Collar 62 is then pulled slightly forward, rotated, and released, allowing pin 70 to retrace through J-groove 72, and allowing return spring 68 to return collar 62 to its rear position abutting motor housing 13, thereby locking the new disposable surgical implement assembly B in place.

While the particular Portable Power Cutting Tool as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A system for performing cutting operations during surgery, comprising:
   a housing;
   a motor mounted within said housing, said motor having a rotating output shaft; and
   a plurality of surgical implement assemblies, each of which includes a different surgical implement and a transmission mechanism designed to impart a characteristic mode of motion to said surgical implement, a first said assembly producing rotary motion, a second said assembly producing reciprocating motion, and a third said assembly producing a combination of rotary and reciprocating motion;
   wherein each of said surgical implement assemblies is selectively attachable one-at-a-time by a user to said motor output shaft to perform a different desired cutting operation using said different surgical implement and said mode of motion which is characteristic to said selected assembly.

2. A system for performing cutting operations during surgery, comprising:
   a housing;
   a motor mounted within said housing, said motor having a rotating output shaft;
   a cam follower attached to said housing;
   a plurality of transmission mechanisms, each said mechanism having an output drive shaft, each said mechanism being designed to impart a different mode of motion to its respective drive shaft, and each said mechanism being selectively attachable one-at-a-time by a user to said motor output shaft to product a selected one of said different modes of motion; and
   a surgical implement attached to each said drive shaft;
   wherein said different modes of motion include rotation, reciprocation, and a combination of rotation and reciprocation.

3. A system as claimed in claim 2, wherein a first said transmission mechanism comprises:
   a first transmission body attachable to said housing;
   a first drive piston attachable to said motor output shaft for rotation by said motor output shaft;
   a cam groove on said first drive piston engaging with said cam follower to cause said first drive piston to reciprocate as said first drive piston rotates; and
   a drive shaft attached to said first drive piston for rotation and reciprocation by said first drive piston.

4. A system as claimed in claim 3, wherein a second said transmission mechanism comprises:
   a second transmission body attachable to said housing;
   a second drive piston attachable to said motor output shaft for rotation by said motor output shaft;
   a cam groove on said second drive piston engaging with said cam follower to cause said second drive piston to reciprocate relative to said housing as said second drive piston rotates;
   a second drive shaft attached to said second drive piston for reciprocation by said second drive piston;
   a rotation limiter piston fixedly attached to said second drive shaft;
   wherein said second drive piston is free to rotate relative to said second drive shaft; and
   wherein said rotation limiter piston is constrained by said second transmission body to prevent rotation of said second drive shaft relative to said housing.

5. A system as claimed in claim 4, wherein a third said transmission mechanism comprises;
   a third transmission body attachable to said housing;
   a drive bushing attachable to said motor output shaft for rotation by said motor output shaft;
   a third drive shaft fixedly attached to said drive bushing for rotation by said drive bushing; and
   a reciprocation limiter bushing fixedly attached to said third drive shaft;
   wherein said reciprocation limiter bushing is constrained by said third transmission body to prevent reciprocation of said third drive shaft relative to said housing.

\* \* \* \* \*

UNITED STATES PATENT AND TRADEMARK OFFICE
CERTIFICATE OF CORRECTION

PATENT NO. : 5,490,860
DATED : Febraury 13, 1996
INVENTOR(S) : George H. Middle; Edward A. Evans; Craig Purdy It is certified that error appears in the above-indentified patent and that said Letters Patent is hereby corrected as shown below:

Column 2, line 55, change "or" to --and--.

Column 3, line 9, change "piston" to --bushing--.

Column 3, line 29, change "piston" to --bushing--.

Column 4, line 52, change "mandrel" to --bushing--.

Column 5, line 24, change "bushing" to --mandrel--.

Column 7, line 41, change "piston" to --bushing--.

Column 7, line 44, change "piston" to --bushing--.

Column 8, line 34, change "piston" to --bushing--.

Column 8, line 39, change "piston" to --bushing--.

Column 8, line 40, change "piston" to --bushing--.

Column 9, line 9, change "bushing" to --piston--.

Signed and Sealed this

Sixth Day of August, 1996

Attest:

BRUCE LEHMAN

Attesting Officer        Commissioner of Patents and Trademarks